United States Patent [19]

Sawyer et al.

[11] Patent Number: 5,443,984
[45] Date of Patent: * Aug. 22, 1995

[54] METHOD FOR CULTURING MAMMALIAN CELLS IN A MEDIUM CONTAINING FISH SERUM

[75] Inventors: Evelyn S. Sawyer; Philip J. Sawyer, both of Kennebunkport, Me.

[73] Assignee: Sea Run Holdings, Inc., Kennebunkport, Me.

[*] Notice: The portion of the term of this patent subsequent to Jun. 20, 2012 has been disclaimed.

[21] Appl. No.: 361,763

[22] Filed: Dec. 22, 1994

Related U.S. Application Data

[63] Continuation of Ser. No. 263,250, Jun. 21, 1994, Pat. No. 5,401,654, which is a continuation-in-part of Ser. No. 168,865, Dec. 16, 1993, abandoned.

[51] Int. Cl.$^6$ .................. C12N 5/00; A61K 35/56; A61K 35/60
[52] U.S. Cl. .................. 435/240.2; 435/240.3; 435/240.21; 424/529; 424/531
[58] Field of Search ............. 435/240.2, 240.21, 240.3, 435/240.31; 424/529, 531

[56] References Cited

U.S. PATENT DOCUMENTS

| | | | |
|---|---|---|---|
| T102,602 | 1/1983 | Isom et al. | 119/4 |
| 4,449,480 | 5/1984 | Isom et al. | 119/4 |
| 4,454,227 | 6/1984 | Roder | 435/240 |
| 5,024,947 | 6/1991 | Inlow et al. | 435/240.31 |

OTHER PUBLICATIONS

Avella et al., In Vitro Cell & Dev. Bio., 30A (1), pp. 41–49 (1994).
Clark et al., In Vitro Cell & Dev. Bio., 23 (6), pp. 417–421 (1987).
ATCC Catalogue of Cell Lines & Hybridomas, 6th Ed., 1988, pp. 342–355.
Jokoby et al., "Methods in Ezymology", vol. LVIII, 1979, Academic Press Inc., pp. 44–93, see entire document.
In Vitro Cellular & Development Biology, vol. 25, No. 9 Sep. 1989, Chou. et al., "Isolation of Melanized Cell Lines with Stable Phenotypes From a Goldfish Erythrophoroma Cell Line And Cryopreservation of These Cells by the Use of Autologous Serum", pp. 813–820, see entire document.
Parasitol Res., vol. 77, No. 8, 1991, Hamers et al, "In Vitro Study of the Impact of Fish Sera on the Survival and Fine Structure of the Eel-Pathogenic Acanthocephalan *Paratenuisentis ambiguus*", pp. 703–708, see entire document.
Cell Differentation and Development, vol. 28, No. 2, Nov. 1989, Chou et al., "Reversible Dedifferentiation and Redifferentiation of a Melanized Cell Line from a Goldfish Tumor", pp. 105–117, see entire document.
"Manufacturers Warned Not to Use Bovine Origin Materials from BSE Countries" FDA Veterinarian, Mar./Apr. 1994.

*Primary Examiner*—Marian C. Knode
*Assistant Examiner*—Susan M. Dadio
*Attorney, Agent, or Firm*—Thomas M. Champagne; John L. Roberts; Roberts & Associates

[57] ABSTRACT

A method for culturing mammalian cells using fish serum. The method uses serum extracted from the blood of fishes to culture mammalian cells for various purposes. The technique has the key advantages of 1) freedom from mammalian infectious agents that could contaminate cell lines or endanger researchers or recipients of therapeutants derived from mammalian cell culture; 2) consistent and reproducible serum content and quality; 3) low cross-reactivity; and 4) provision of the appropriate serum nutrients to maintain the growth of mammalian cells. Fish serum is used together with designated defined media to allow mammalian cells to grow and populations of these cells to be maintained. Blood serum is derived from captive stocks of fish raised under controlled conditions such that the diet, habitat, genetics, life history, and reproductive status of the fish remains substantially consistent and reproducible.

8 Claims, No Drawings

METHOD FOR CULTURING MAMMALIAN CELLS IN A MEDIUM CONTAINING FISH SERUM

This is a continuation of U.S. patent application Ser. No. 08/263,250, filed Jun. 21, 1994, which was a continuation-in-part of U.S. Pat. application Ser. No. 08/168,865, filed Dec. 16, 1993, now abandoned.

FIELD OF THE INVENTION

The present invention relates generally to cell culture, and more specifically to the culture of mammalian cells using a serum derived from fish. The technique has significant advantages over the more commonly used technique of using blood serum derived from fetal calves or other mammals as more fully set forth below.

BACKGROUND OF THE INVENTION

Animal cell culture is a basic technique in the fields of biology and medicine. The production of living cells in vitro, in the laboratory, permits numerous applications that would be difficult or impossible in vivo, in the living animal. The culture of animal cells requires a defined medium containing specific quantities of certain chemicals, and in addition for most cells, up to 15% of an undefined nutrient medium usually fetal bovine serum (FBS). Serum from newborn calves and other mammals is also used, but FBS is preferred because of its high level of growth factors and low cross-reactivity with other animal cells. FBS or other mammalian products are also used to coat the surface of culture-ware to promote cell attachment.

The production of FBS in this country is an estimated 700,000 liters annually worth $300 to $400 million. The industry obtains fetal calves for bleeding from slaughter houses, or in some cases, rears herds of cattle for this purpose. These herds are held in as isolated a situation as possible in order to prevent disease. Whole blood is obtained aseptically (by syringe) from an animal, centrifuged to separate cells from serum, and the serum filtered to 0.22 microns to remove most bacteria. Often, serum is heated to 56° C. to inactivate the complement system, a group of immune proteins.

Contamination of cell cultures because of infectious organisms in serum can be a serious problem. Bacteria, fungi, viruses, and mycoplasma have been isolated from bovine serum. In the period from 1960–1980, mycoplasma from bovine serum was the second major group of contaminants found in cell culture (Barile, 1977). Now, FBS is usually screened for mycoplasma and most viruses. However, a more serious cause for concern is an all-protein infectious agent called a prion for which no test is available (Kingman, 1993). This organism causes a fatal brain disease in mammals called Bovine Spongiform Encephalopathy (BSE), or "mad cow disease". BSE occurs in sheep, cows, and other mammals, and is most likely the cause of similar neurodegenerative diseases in humans. In Britain in 1986, BSE resulted in the destruction of cattle and caused fears for the safety of the meat supply and other bovine products. Since then, the disease has turned up in cattle in many other countries. Consequently, serum from these countries cannot be imported for use in the U.S.

Basic texts in cell culture teach a like-for-like approach, or mammalian sera, especially FBS, for culture of mammalian cells (Freshney, 1986). So firmly established is this dogma of FBS, that some cell culture publications refer only to "serum", when FBS is intended (Pollard and Walker, 1984). Likewise, major serum suppliers such as Sigma Chemical Co. and Hy-Clone Laboratories include only bovine and some equine sera in their cell culture catalogs. In practice during the past thirty years, only mammalian sera have been used for the culture of mammalian cells.

U.S. Pat. No. 4,449,480 to Isom et al. discloses freshwater mussels in an artificial habitat utilizing growth media. However, the Isom et al. invention is directed to larviculture, that is, the provision of food and habitat for the larval stage of young animals such as aquatic invertebrates. Isom et al. are not concerned with cell culture. Larviculture is an interim technique, having the goal of keeping the larval animal alive until it can progress to the next stage, or in this particular case, until it can transform from a parasitic stage and feed independently on its own (Pennack 1953). Thus, the Isom et al. invention is not applicable to the instant problem, as cell lines do not grow and transform to become independent of their culture medium and learn to feed on their own.

Further, the method taught by Isom et al. can only operate on the parasitic stage of whole, multicellular animals (Barnes, 1963), and is not applicable to cell lines derived from the organs and tissues of a whole animal. A fundamental purpose of cell culture is to permit processes and experimentation in cells that would not be possible to perform on a whole animal. Isom et al. borrow certain techniques from cell culture (for example, a modified solution or medium of salts and proteins) and from bacteriology (for example, antibiotics). The use of these tools, however, does not render the Isom et al. method a cell culture or bacteriology process, and the disclosed method cannot function as such. Thus, the Isom et al. method cannot provide a solution to the instant problem.

SUMMARY OF THE INVENTION

It is therefore an object of the present invention to provide a method of using fish serum to culture mammalian cells.

It is a further object of the present invention to use a serum for mammalian cell culture that is free from various mammalian infectious agents, such as BSE, that could endanger researchers or the recipients of cell culture products.

It is another object of the present invention to provide a serum for cell culture that is free from mammalian infectious agents that can invalidate the results of scientific testing relating to the culture of mammalian cells.

It is a further object of the present invention to create a new serum supply of consistent quality for use in cell culture.

It is still a further object of the present invention to provide a means to enhance the supply of serum that is available for research and commercial production in the biotechnology field specifically for the culture of mammalian cells.

These and other objects and advantages of the present invention will be apparent to those of ordinary skill in the art upon inspection of the detailed description, drawings, and appended claims.

The present invention is a method of using fish serum instead of bovine or other mammalian sera for mammalian cell culture. This method would appear contradictory to those skilled in the art of cell culture. Because of the great phylogenetic differences between fish and mammals, there is a reasonable expectation of failure. Searches of the non-patent literature show no prior use of fish serum for mammalian cell culture.

The mammalian cell lines used in the method of the present invention are commonly used for a number of experimental and commercial applications. These applications include toxicology, biochemistry, cancer research, and the production of recombinant proteins for therapy in humans and domestic animals. There is growing concern that these therapeutants could carry the infectious organisms found in bovine serum (Anon. 1994). Therefore, the use of fish serum instead of mammalian serum in the culture of these cells provides important safety advantages for the recipients of these recombinant products.

Fish serum can be used for cell culture applications that now employ bovine or other mammalian sera, and for applications where these sera are ineffective or unsafe.

The ideal serum for mammalian cell culture would provide the nutrients and growth factors that maintain mammalian cells and support their growth. In addition, the serum should be (A) consistent in quality, (B) have serum immune proteins (immunoglobulins), either at very low levels (as in FSB) or unlike those of mammals for low cross-reactivity, and (C) be free of mammalian infectious agents that would contaminate cell lines cell culture products, or endanger researchers.

It has been found that serum from fishes is effective for mammalian cell culture, and meets the characteristics of the ideal serum with respect to consistency, low cross-reactivity, safety, and control of content.

A. Consistency

Until the past few years, serum from fish would have been inconsistent in quality, because wild stocks (even within the same species) vary in diet, habitat, genetics, life history, and reproductive status. This inconsistency would influence the reproducibility of cell culture experiments, and make fish serum unsuitable for cell culture research. Now, by using domesticated stocks reared in aquaculture facilities, fish serum can be obtained with product consistency similar to serum from herds of cattle reared for this purpose. The essential requirement is for donor fish to be reared under consistent and therefore reproducible conditions, not necessarily the nature or specifics of these conditions. This reproducibility of conditions reduces variability in serum content, and yields lot-to-lot consistency of serum - an important factor in cell culture.

The preferred specific rearing conditions for the donor fish are disclosed in the Detailed Description of the Present Invention. However, other conditions are desirable to alter a component in fish serum for culture of specific mammalian cells, as described below.

B. Low Cross-Reactivity

The fishes are a distinct evolutionary group from the mammals. As such, many of their enzyme and immune system proteins, especially immunoglobulins, differ from those of mammals. Most fishes are cold-blooded vertebrates having a body temperature that approximates that of the waters where they live. Cold water fishes normally live in water with a temperature range of 0° C. to 18° C., and do not survive long above 20° C. Therefore, their serum proteins, including antibody proteins, function within a range far below the 37° C. and higher body temperatures characteristic of the warm-blooded vertebrates such as humans and other mammals. This functional temperature difference strongly implies a difference in protein structure.

C. Safety

Both evolutionary and temperature differences provide important safety qualities to fish serum. Very few bacteria or viruses that infect live fishes can infect mammals. Instead, viruses of cold-water fishes are often controlled by raising water temperature (and therefore the fishes' body temperature) above 18° C. (Wolf, 1988). Therefore, infection of mammalian cell cultures or of researchers by an agent in fish serum is highly unlikely.

D. Control of Content

An additional advantage of using fish serum for cell-culture applications is control of serum content. Levels of certain substances in fish serum can be controlled by procedures that would be impossible with mammals for biological or regulatory reasons. For example, mammalian genetic triploids are not viable, but in salmonids, triploids live and grow normally and serum from the female triploid contains no sex steroids (Schreck and Moyle, 1990). Conversely, the sexual maturity of donor fish can be induced by light or hormone injections if high sex steroid serum is desired. Also, fish can be held under conditions unacceptable for mammals, such as total darkness, to increase certain hormones such as melatonin in serum.

DETAILED DESCRIPTION OF THE PRESENT INVENTION

Using the present invention, the culture of two commonly used lines of mammalian cells in fish serum has been demonstrated. The cell lines used were Chinese hamster ovary cells (CHOs), supplied by the ATCC (#CCL-61), and monkey kidney cells (VEROs), also supplied by the ATCC #CCL-81. The fish serum used was taken from two species of salmonids, the rainbow trout and the steelhead (*Oncorhynchus mykiss*), and the Atlantic salmon (*Salmo salar*), the lumpfish (*Cyclopterus lumpus*), and the channel catfish (*Ictalurus punctatus*). These species were used because consistent and reproducible methods for their production are well established, large numbers of these species are reared in commercial aquaculture and therefore large amounts of serum can be obtained, and individual fish are large enough (over two pounds) so that blood can be drawn easily. Other species of aquacultured fish fit these criteria, particularly the sturgeon and the striped bass.

The process begins with the consistent and reproducible conditions in which donor fish are reared. All fish used as serum sources are 1) progeny of domesticated broodstock, 2) inspected for disease according to the American Fisheries Society Blue Book standards, 3) sexually immature, 4) in the log phase of growth, 5) larger than two pounds (range from 2–12 pounds), 6) reared by standard husbandry methods appropriate to the species as described in Piper (1988), and 7) fed commercially manufactured pelleted feed of a composition consistent with that recommended by Halver (1972) and commonly used for each species. Rainbow trout and catfish are reared in freshwater; steelhead, salmon and lumpfish are reared in seawater.

Water temperature at the time of bleeding is normally 8° to 12° C., but water temperatures of 4° to 14° C. are suitable for rainbow trout, salmon, steelhead, and lumpfish, and temperatures of 4° to 30° C. for catfish; the objective being to avoid handling stress in the donor fish. Handling stress is further reduced by starving fish for 48 hours before bleeding.

Each fish is stunned by administering a sharp blow to said fish's head, by immersion in ice-water, or by immersion in water containing $CO_2$ or other fish anesthetic, the objective being to stun the fish to a level of loss of reflex activity (loss of consciousness) as defined by Schreck and Moyle (1990). Whole blood is then drawn by syringe from the dorsal aorta, or the caudal vein. No more than 20% of the fish's total blood volume is drawn at each bleeding. After a recovery time of approximately two weeks, the same fish can be bled again. Repeated bleeding of the same group of fish (up to the time they become sexually mature) results in low lot-to-lot variability in the serum. Serum parameters for all fish species used and a comparison sample of FBS are given in Table 1. For the method described, fish serum content must fall within the range given in Table 1.

TABLE 1

Serum Analysis

| Compound | Fish Serum | Amount | Fetal Bovine Serum* |
|---|---|---|---|
| Glucose | 50–100 | mg/dL | 92 |
| Blood urea nitrogen | 1–3 | mg/dL | 18 |
| Creatinine | 0.3–3 | mg/dL | 2.8 |
| Sodium | 130–170 | mEq/dL | 135 |
| Chloride | 130–140 | mEq/dL | 96 |
| Calcium | 10–18 | mg/dL | 14 |
| Phosphorus | 10–20 | mg/dL | 11 |
| Uric acid | 0.2–2 | mg/dL | 1.8 |
| Total protein | 3–6 | g/dL | 3.5 |
| Albumin | 0.5–2.8 | g/dL | 2.6 |
| Globulin | 0.6–3.6 | g/dL | 0.9 |
| Bilirubin | 0.1–1 | mg/dL | 0.1 |
| Iron | 20–100 | ug/dL | 191 |
| Cholesterol | 300–500 | mg/dL | 39 |
| Triglycerides | 300–600 | mg/dL | 74 |

*FBS lot obtained from Sigma Chemical Co.

Blood is allowed to clot for not less than 15 minutes or more than 2 hours, and is then centrifuged at $1100 \times g$ for at least 10 minutes and for no more than 20 minutes.

Serum is removed from the collection tubes and sterilized by passing first through a $0.45\mu$ filter, and then through a $0.22\mu$ filter.

Serum from 6 or more fish of the same species is combined as a numbered lot, and frozen at $-70°$ C. No heat treatment such as that commonly used for bovine serum to denature complement immune system proteins is needed.

CHO or VERO cells shipped frozen from the American Type Culture Collection are thawed, counted, and seeded immediately in 25 cm² sterile tissue culture flasks containing 5.0 ml of medium. The medium is RPMI-1640, a widely-used defined medium (which may be purchased from Sigma Chemical Co.), plus 10% (v/v) FBS. This flask containing cells and medium is placed in an incubator at 37° C. and 5% $CO_2$. Cells are allowed to grow and increase in numbers over a period of one week. During this time, the cells are "split" or subcultured every 48 hours as follows. After the first 48 hours, cells from the original flask are detached using the standard trypsinization technique described by Pollard and Walker (1984) and are transferred to two new 25 cm² tissue culture flasks. This procedure is repeated every 48 hours until a total of eight flasks have been seeded.

Cells growing in 10% FBS must be adapted first to lower levels of FBS before they can be cultured in similar low levels of fish serum.

When the cells in the eight flasks have reached the log phase of growth, the process of weaning to lower FBS levels begins. The RPMI-1640 plus 10% FBS is removed by aspiration or pipette from each flask, and replaced with RPMI-1640 plus 7.5% FBS. These flasks are placed in the incubator and the cells are allowed to grow and increase in number for 48 hours. At this time the RPMI-1640 with 7.5% FBS is removed from the eight flasks and replaced with RPMI-1640 plus 5% FBS. The process may be repeated to lower FBS levels to 2.5% or 1%. The weaning process takes up to 10 days to acclimate cells to the lower concentrations of FBS.

Cells growing in the flasks containing RPMI-1640 plus 5% or 2.5% or 1% FBS are then harvested using standard trypsinization techniques, washed with serum-free RPMI-1640, centrifuged at 300 g for 3.5 minutes at room temperature, counted in a hemocytometer, and resuspended in new 25 cm² tissue culture flasks containing serum-free RPMI-1640. Aliquots from these flasks containing $5 \times 10^4$ cells/ml (by calculation) are then seeded in new flasks containing 5 ml of RPMI-1640 plus thawed fish serum as described above, at a concentration of 2.5% or 5% (v/v). Flasks containing the cells and media are then incubated at 37° C. in 5% $CO_2$/95% air.

At these concentrations of fish serum, cells will grow normally with an approximate doubling time of 24 hours, the same as would be expected if they were cultured in FBS. When the cells are stained with a hematoxylin stain for observation, those cultured with 1% or 2.5% fish serum are normal and qualitatively similar to those cultured in media containing FBS (FIG. 1.). Cells cultured at 5% fish serum appear normal except for small lipid-filled vacuoles in the cytoplasm.

At this stage, CHOs or VEROs can be subcultured for experimental or commercial purposes using fish serum as a replacement for FBS, in either flasks or suspension culture.

Preferred and alternate embodiments have now been described in detail. It is to be noted, however, that this description is merely illustrative of the principles underlying the inventive concept. It is therefore contemplated that various modifications of the disclosed embodiments will, without departing from the spirit and scope of the present invention, be apparent to those of ordinary skill in the art. For example, other species of fish and other mammalian cells may be substituted for those disclosed herein.

The species of fish used as a source of serum may vary depending on what mammalian cells are to be cultured. However, the reproducibility of fish species and strain used and of fish culture conditions required for consistent serum quality limits donor species to those grown in aquaculture. Content of serum is influenced by such factors as husbandry, feed, reproductive status, genetics, age, and handling. Also, some fishes containing trimethyl amine oxide or high levels of other non-protein nitrogen (ammonia or amines) in their serum may be unsuitable as donors.

The method of obtaining the serum is not critical as long as the fish are treated in a humane manner and serum is obtained and processed (centrifuged, filtered, packaged, etc.) aseptically.

Although the method is described using CHOs and VEROs, later experimentation has shown that normal diploid fibroblasts can be cultured using the fish serum method.

For CHOs, VEROs, or other cell lines, the defined medium (RPMI-1640) may be replaced with other media selected from the group consisting of Eagles MEM, BME, Medium 199, or McCoys, all widely-used defined media.

The apparent limitation of no more than 5% fish serum for culturing mammalian cells is most likely the result of the very high levels of lipid in the sera of most bony fishes (Teleosts). Such a large excess of any essential component in the cell culture media is likely to be inhibitory. Cholesterol levels of 300-500 mg/dL and triglycerides of 300-600 mg/dL were routinely measured in the sera of the bled fishes. This compares with cholesterol of 30-60 mg/dL and triglycerides of 50-80 mg/dL in FBS. Lowering lipid levels in fish serum through physical or chemical removal or changes in fish diet would most likely remove the 5% limitation.

References

Anonymous, 1994. "Manufacturers warned not to use bovine-origin materials from BSE countries". *FDA Veterinarian*, Mar./Apr. 1994, page 8.

Barile, M. F. 1977. "Mycoplasma Contamination of Cell Cultures - a Status Report". *Cell Culture and its Applications* (R. T. Acton and J. D. Lynn, Eds.) pages 291-334.

Barnes, R. D. 1963. *Invertebrate Zoology*. W. B. Saunders Co. Philadelphia, Pa. pages 297-298.

Freshney, R. I. 1987. *Animal Cell Culture - A Manual of Basic Techniques*. J. Wiley & Sons, N.Y.

Halver, J. E. 1972 *Fish Nutrition*. Academic Press, New York.

Kingman, S. 1993. "London Meeting Explores the Ins and Outs of Prions". *Science* 262 : 180-181.

Pennak, R. W. 1953. *Freshwater Invertebrates of the United States*.

Piper, R. G. 1983. *Fish Hatchery Management*. U.S. Department of the Interior, Fish and Wildlife Service. Washington, D.C.

Pollard, J. W. and Walker, J. M. 1990. "Basic Cell Culture". *Methods in Molecular Biology*, Volume 5; Animal Cell Culture. Humana Press, Clifton, N.J. pages 1-12.

Schreck, C. B. and Moyle, P. B., 1990. *Methods in Fish Biology*, pp. 223-232. American Fisheries Society, Bethesda, Md. Wolf, K. 1988. *Fish Viruses and Fish Viral Disease*, p. 108. Cornell University Press, Ithaca, N.Y.

We claim:

1. A method of culturing mammalian cells comprising the steps of:
   (a) seeding mammalian cells in a vessel containing a defined cultured medium and 10% fetal bovine serum;
   (b) culturing the cells of step (a);
   (c) subculturing the cells of step (b) in a vessel containing a defined culture medium and 10% fetal bovine serum;
   (d) removing the defined culture medium and fetal bovine serum from the vessel of step (c);
   (e) adding defined culture medium with a lower concentration of fetal bovine serum to the vessel of step (d);
   (f) harvesting the cells of step (e);
   (g) suspending the cells of step (f) in a defined culture medium;
   (h) centrifuging the cells of step (g) at 300 g for about 3.5 minutes at room temperature;
   (i) resuspending the cells of step (h) in a vessel containing defined culture medium;
   (j) seeding at least a portion of the cells of step (i) in a vessel containing a defined culture medium and about 2.5% to about 5% fish serum;
   wherein said fish serum is prepared by:
      (i) raising fish under controlled conditions such that the diet, habitat, genetics, life history, and reproductive status of the fish remains substantially constant and reproducible;
      (ii) starving the fish for up to about forty-eight hours;
      (iii) withdrawing whole blood from the fish;
      (iv) separating the serum from the whole blood; and
      (iv) sterilizing the serum;
   and,
   (k) culturing the cells of step (k).

2. The method of claim 1, wherein step (e) comprises:
   (aa) adding defined culture medium and 7.5% fetal bovine serum to the vessel of step (d);
   (bb) culturing the cells of step (aa);
   (cc) subculturing the cells of step (bb);
   (dd) removing the defined culture medium and fetal bovine serum from the vessel of step (cc);
   (ee) adding defined culture medium and 5% fetal bovine serum to the vessel of step (dd).

3. The method of claim 1, wherein step (e) comprises:
   (aa) adding defined culture medium and 7.5% fetal bovine serum to the vessel of step (d);
   (bb) culturing the cells of step (aa);
   (cc) subculturing the cells of step (bb);
   (dd) removing the defined culture medium and fetal bovine serum from the vessel of step (cc);
   (ee) adding defined culture medium and 5% fetal bovine serum to the vessel of step (dd);
   (ff) culturing the cells of step (ee);
   (gg) subculturing the cells of step (ff);
   (hh) removing the defined medium and fetal bovine serum from the vessel of step (gg);
   (ii) adding defined culture medium and 2.5% fetal bovine serum to the vessel of step (hh).

4. The method of claim 1, wherein step (e) comprises:
   (aa) adding defined culture medium and 7.5% fetal bovine serum to the vessel of step (d);
   (bb) culturing the cells of step (aa);
   (cc) subculturing the cells of step (bb);
   (dd) removing the defined culture medium and fetal bovine serum from the vessel of step (cc);
   (ee) adding defined culture medium and 5% fetal bovine serum to the vessel of step (dd);
   (ff) culturing the cells of step (ee);
   (gg) subculturing the cells of step (ff);
   (hh) removing the defined medium and fetal bovine serum from the vessel of step (gg);
   (ii) adding defined culture medium and 2.5% fetal bovine serum to the vessel of step (hh);
   (jj) culturing the cells of step (ii);
   (kk) subculturing the cells of step (jj);
   (ll) removing the defined medium and fetal bovine serum from the vessel of step (kk);
   (mm) adding defined culture medium and 1% fetal bovine serum to the vessel of step (ll).

5. A method of culturing mammalian cells comprising:
   (a) seeding mammalian cells in a vessel containing a defined cultured medium and 10% fetal bovine serum;
   (b) culturing the cells of step (a);

(c) subculturing the cells of step (b) in a vessel containing a defined culture medium and 10% fetal bovine serum;

(d) removing the defined culture medium and fetal bovine serum from the vessel of step (c);

(e) adding defined culture medium with a lower concentration of fetal bovine serum to the vessel of step (d);

(f) harvesting the cells of step (e);

(g) suspending the cells of step (f) in a defined culture medium;

(h) centrifuging the cells of step (g) at 300 g for about 3.5 minutes at room temperature;

(i) resuspending the cells of step (h) in a vessel containing defined culture medium;

(j) seeding at least a portion of the cells of step (i) in a vessel containing a defined culture medium and about 2.5% to about 5% thawed, fish serum; wherein said fish serum is prepared by:

(i) raising fish under controlled conditions such that the diet, habitat, genetics, life history, and reproductive status of the fish remains substantially constant and reproducible;

(ii) starving the fish for up to about forty-eight hours;

(iii) withdrawing whole blood from the fish;

(iv) separating the serum from the whole blood;

(iv) sterilizing the serum; and (v) freezing the serum;

and, (k) culturing the cells of step (k).

6. The method of claim 5, wherein step (e) comprises:

(aa) adding defined culture medium and 7.5% fetal bovine serum to the vessel of step (d);

(bb) culturing the cells of step (aa);

(cc) subculturing the cells of step (bb);

(dd) removing the defined culture medium and fetal bovine serum from the vessel of step (cc);

(ee) adding defined culture medium and 5% fetal bovine serum to the vessel of step (dd).

7. The method of claim 5, wherein step (e) comprises:

(aa) adding defined culture medium and 7.5% fetal bovine serum to the vessel of step (d);

(bb) culturing the cells of step (aa);

(cc) subculturing the cells of step (bb);

(dd) removing the defined culture medium and fetal bovine serum from the vessel of step (cc);

(ee) adding defined culture medium and 5% fetal bovine serum to the vessel of step (dd);

(ff) culturing the cells of step (ee);

(gg) subculturing the cells of step (ff);

(hh) removing the defined medium and fetal bovine serum from the vessel of step (gg);

(ii) adding defined culture medium and 2.5% fetal bovine serum to the vessel of step (hh).

8. The method of claim 5, wherein step (e) comprises:

(aa) adding defined culture medium and 7.5% fetal bovine serum to the vessel of step (d);

(bb) culturing the cells of step (aa);

(cc) subculturing the cells of step (bb);

(dd) removing the defined culture medium and fetal bovine serum from the vessel of step (cc);

(ee) adding defined culture medium and 5% fetal bovine serum to the vessel of step (dd);

(ff) culturing the cells of step (ee);

(gg) subculturing the cells of step (ff);

(hh) removing the defined medium and fetal bovine serum from the vessel of step (gg);

(ii) adding defined culture medium and 2.5% fetal bovine serum to the vessel of step (hh);

(jj) culturing the cells of step (ii);

(kk) subculturing the cells of step (jj);

(ll) removing the defined medium and fetal bovine serum from the vessel of step (kk);

(mm) adding; defined culture medium and 1% fetal bovine serum to the vessel of step (ll).

* * * * *